United States Patent [19]

Hayes et al.

[11] Patent Number: 5,010,096
[45] Date of Patent: Apr. 23, 1991

[54] METHOD OF PROTECTING MAMMALS AGAINST NEURONAL DAMAGE RESULTING FROM CEREBRAL ISCHEMIA

[75] Inventors: Ann G. Hayes, Potters Bar; Phillip J. Birch, Biggleswade, both of England

[73] Assignee: Glaxo Group Limited, London, England

[21] Appl. No.: 443,189

[22] Filed: Nov. 30, 1989

[30] Foreign Application Priority Data

Dec. 1, 1988 [GB] United Kingdom ............... 8828032

[51] Int. Cl.$^5$ .............................................. A61K 31/40
[52] U.S. Cl. .................................... 514/411; 514/921; 514/452; 514/906; 514/930
[58] Field of Search ............... 514/411, 452, 906, 930, 514/921

[56] References Cited

U.S. PATENT DOCUMENTS 4,496,579 1/1985 Crame et al. ..................... 514/411
4,769,367 9/1988 Cherry et al. ..................... 514/217
4,880,801 11/1989 Kitchin et al. .................... 514/215

FOREIGN PATENT DOCUMENTS 2174087 10/1986 United Kingdom .

OTHER PUBLICATIONS

Gustafson et al., Cerebrovascular Diseases; 1989, 117.
Gustafson et al., J. Cerebral Flow Metab., 1989, 1.
C. A. Halliday et al., Br. J. Pharmacol., 1989, 95 (Suppl.), 857P.
C. A. Halliday et al., Br. J. Pharmacol., 1988, 95 (Suppl.), 751P.
R. Seitelberger et al., Circ. Res., 1988, 62(3), 436.

Primary Examiner—Stanley J. Friedman
Assistant Examiner—Terry L. Wilson
Attorney, Agent, or Firm—Morgan & Finnegan

[57] ABSTRACT

The use of a compound of formula (I) or a physiologically acceptable salt or hydrate thereof in the treatment, relief or prevention of the effects of cerebral ischaemia

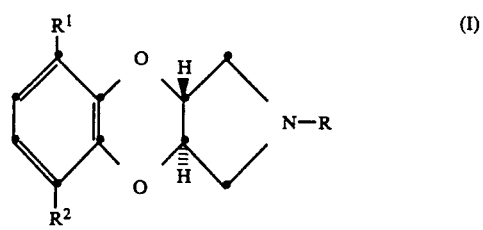

Compounds of formula (I) are described in UK Published Patent Application No. 2157691A.

The compounds of formula (I) have been found to protect mammals, including man, against neuronal damage resulting from cerebral ischaemia.

The preferred compound for use in this indication is ($\pm$)-trans-5-fluoro-2,3,3a,9a-tetrahydro-1H-[1,4]-benzodioxino[2,3-c]- pyrrole (formula (I), R=H, R$^1$=F, R$^2$=H), especially in the form of its hydrochloride salt.

8 Claims, No Drawings

METHOD OF PROTECTING MAMMALS AGAINST NEURONAL DAMAGE RESULTING FROM CEREBRAL ISCHEMIA

This invention relates to a new medical use for certain heterocyclic compounds and to pharmaceutical compositions containing them. In particular it relates to the use of the benzodioxinopyrrole compounds disclosed in published UK Patent Application No. 2157691A and physiologically acceptable salts and hydrates thereof in treating, relieving or preventing the effects of cerebral ischaemia.

Published UK Patent Application No. 2157691A discloses compounds which may be represented by the formula (I)

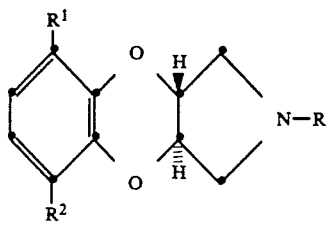
(I)

wherein
R is a hydrogen atom or a group selected from $C_{1-6}$ alkyl (optionally substituted by $C_{3-7}$ cycloalkyl), $C_{3-6}$ alkenyl, $C_{3-6}$ alkynyl, $C_{3-7}$ cycloalkyl aralkyl (in which the alkyl moiety contains 1-5 carbon atoms) and —CHO; $R^1$ is a halogen atom or a group selected from $C_{1-4}$alkyl, $C_{1-4}$alkoxy, hydroxyl, cyano, nitro and —$NR^3R^4$ where $R^3$ and $R^4$ is each a hydrogen atom or a $C_{1-4}$alkyl group; and
$R^2$ is a hydrogen atom, a halogen atom or is a group as defined above for $R^1$;
and the physiologically acceptable salts and hydrates thereof.

In general formula (I), the alkyl, alkenyl and alkynyl groups represented by R, $R^1$ and $R^2$ may be straight or branched chain groups.

When R contains a —C=C— or —C≡C— linkage this is not directly attached to the nitrogen atom. When R is alkyl it may be, for example, methyl, ethyl or propyl, methyl being preferred. When R is an alkyl group substituted by a $C_{3-7}$ cycloalkyl group it may be for example, cyclopropyl$C_{1-3}$alkyl such as cyclopropylmethyl. When R is alkenyl it may be, for example, allyl and when R is alkynyl it may be, for example, propynyl. When R is cycloalkyl it may be, for example, cyclopropyl. When R is an aralkyl group it may be, for example phen$C_{1-5}$alkyl, such as benzyl.

The halogen atoms represented by $R^1$ and $R^2$ may be fluorine, chlorine, bromine or iodine atoms. Examples of alkyl and alkoxy groups represented by $R^1$ and $R^2$ are methyl, ethyl, methoxy and ethoxy groups. The group —$NR^3R^4$ may be, for example, an amino, methylamino, ethylamino, dimethylamino or diethylamino group.

Suitable physiologically acceptable salts disclosed are the acid addition salts formed with inorganic acids, for example hydrochlorides, hydrobromides, phosphates and sulphates, and with organic acids, for example citrates, tartrates, acetates, maleates and succinates.

It will be appreciated that each compound of formula (I) is a trans isomer and exists as two enantiomers. The structural formulae herein are to be understood to depict either enantiomer of each compound as well as mixtures, including racemates, even though the precise structure as set out relates only to one enantiomer.

The compounds disclosed in the aforementioned patent specification are described as selective $\alpha_2$-adrenoreceptor antagonists of interest in the treatment or prevention of migraine, thrombosis, diabetes, obesity, hypertension, constipation, paralytic ileus, senile dementia and in particular for the treatment of depression.

We have now found that compounds of formula (I) are also of use in protecting against neuronal damage resulting from cerebral ischaemia which may be demonstrated in animals using, for example, the gerbil bilateral carotid occlusion model or the rat two vessel occlusion plus hypotension model described below. Compounds of formula (I) and their physiologically acceptable salts or hydrates are therefore useful in treating, relieving or preventing the effects of cerebral ischaemia.

According to one aspect of the invention we therefore provide a compound of formula (I) or a physiologically acceptable salt or hydrate thereof for use in treating, relieving or preventing the effects of cerebral ischaemia.

In an alternative or further aspect the invention provides a method of treatment of a mammal including man, suffering from or susceptible to the effects of cerebral ischaemia which comprises administering an effective amount of a compound of formula (I) or a physiologically acceptable salt or hydrate thereof.

It will be appreciated that whilst compounds of formula (I) will primarily be of use in the alleviation of established symptoms, prophylaxis is not excluded.

In a further aspect the invention provides a compound of formula (I) or a physiologically acceptable salt or hydrate thereof for use in the manufacture of a medicament for treating, relieving or preventing the effects of cerebral ischaemia.

A preferred compound of formula (I) for use according to the present invention is ($\pm$)-trans-5-fluoro-2,3,3a,9a-tetrahydro-1H-[1,4]-benzodioxino [2,3-c]pyrrole, which may be represented by the formula (II)

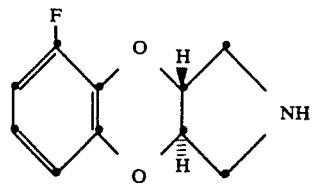
(II)

and its physiologically acceptable salts and hydrates. A preferred form of the compound (II) for use according to the invention is the hydrochloride, particularly in hydrated form, for example as the hemihydrate.

Compounds for use according to the invention may be administered as the raw material but the active ingredient is preferably presented as a pharmaceutical formulation. The active ingredient may conveniently be presented in unit dose form.

Compounds of formula (I) for use according to the invention may be formulated in a conventional manner using one or more pharmaceutically acceptable carriers or excipients for administration by any convenient route, for example for oral rectal or parenteral administration. Compounds for use according to the invention may conveniently be formulated for oral or parenteral administration.

For oral administration, the pharmaceutical compositions may take the form of for example, tablets or capsules prepared by conventional means with pharmaceutically acceptable excipients such as binding agents (for example pregelatinised maize starch, polyvinylpyrrolidone or hydroxypropyl methylcellulose); fillers (for example lactose, microcrystalline cellulose or calcium phosphate); lubricants (for example magnesium stearate, talc or silica); disintegrants (for example potato starch or sodium starch glycollate); or wetting agents (for example sodium lauryl sulphate). The tablets may be coated by methods well known in the art. Liquid preparations for oral administration may take the form of for example, solutions syrups or suspensions, or they may be presented as a dry product for constitution with water or other suitable vehicle before use. Such liquid preparations may be prepared by conventional means with pharmaceutically acceptable additives such as suspending agents (for example sorbitol syrup, methyl cellulose or hydrogenated edible fats); emulsifying agents (for example lecithin or acacia); non-aqueous vehicles (for example methyl or propyl-p-hydroxybenzoates or sorbic acid).

The compounds for use according to the invention may be formulated for parenteral administration by injection, conveniently intravenous or subcutaneous injection, for example by bolus injection or continuous intravenous infusion. Formulations for injection may be presented in unit dosage form, for example, in ampoules or in multi-dose containers, with an added preservative.

The compositions may take such forms as suspensions, solutions or emulsions is oily or aqueous vehicles, and may contain formulatory agents such as suspending, stabilising and/or dispersing agents. Alternatively, the active ingredient may be in powder form for constitution with a suitable vehicle, for example sterile pyrogen-free water, before use.

Compositions for rectal administration may be in the form of suppositories using a conventional suppository excipient.

It will be appreciated that the precise dose administered will depend on the age and condition of the patient, the particular compound used, and the frequency and route of administration. The compounds may be administered in single or divided doses and may be administered one or more times, for example 1 to 4 times, per day.

A proposed daily dose of compounds (I) for administration to man for use according to the invention is 0.04 to 40 mg/kg, for example 2 to 12 mg/kg. The daily dose may conveniently be administered in unit dose form, each unit dose containing for example 0.04 to 12 mg/kg of active ingredient.

PHARMACEUTICAL EXAMPLES

In the following example, 'Active Ingredient' refers to (±) trans-5-fluoro-2,3,3a,9a-tetrahydro-1H-[1,4]-benzodioxino[2,3-]pyrrole hydrochloride. Other compounds of the invention may be formulated in similar fashion.

1. Oral Capsule

|  | per capsule |
| --- | --- |
| Active Ingredient | 50 mg |
| Magnesium stearate | 0.5 mg |
| Anhydrous lactose | 50 mg |

Blend the active ingredient with the lactose and magnesium stearate. Fill the blend into appropriate size hard gelatin capsules (lock fitting type) on an automatic capsule filling machine).

2. Oral Syrup

|  | per 5 ml dose |
| --- | --- |
| Active Ingredient | 50 mg |
| Sodium citrate | 25 mg |
| Citric acid | to pH 4.5 |
| Sunset yellow FCF (Dye) | 0.25 mg |
| Methyl hydroxybenzoate sodium | 5.0 mg |
| Propyl hydroxybenzoate sodium | 2.0 mg |
| Liquid orange flavour | qS |
| Sucrose | 3.25 g |
| Purified water | to 5.0 ml |

Dissolve the sucrose in a minimum quantity of water. Add a concentrated solution of sodium citrate with stirring and adjust the pH to 4.5 with citric acid. With continued stirring, add a 10% aqueous solution of the active ingredient followed by a solution of the dye, a solution of the hydroxybenzoates and lastly the flavour. Adjust almost to volume with water and stir. Check the pH and adjust to 4.5 with citric acid if necessary. Make up to volume with water.

3. Oral Tablet

|  | per tablet |
| --- | --- |
| Active Ingredient | 50 mg |
| Polyvinylpyrrolidone | 4.0 mg |
| Sodium starch glycollate | 10.0 mg |
| Magnesium stearate | 2.0 mg |
| Lactose to tablet core weight to | 200 mg |

Blend the active ingredient with the lactose. Add a sufficient quantity of polyvinylpyrrolidone solution to produce a damp mass suitable for granulation. Prepare the granules and dry using a tray or fluid bed dryer. Pass through a sieve, blend with the remaining ingredients and compress into 8 mm diameter tablets on a tablet machine.

Film coat the tablet cores with hydroxypropyl methyl cellulose or similar film forming material, using either an aqueous or non-aqueous solvent system. A plasticizer and suitable colour may be included in the film coating solution.

The two in vivo models (gerbil bilateral carotid occlusion and rat two vessel occlusion plus hypotension set out below are standard tests for testing the efficacy of compounds in protecting against neuronal damage resulting from cerebral ischaemia.

A. Gerbil bilateral carotid occlusion model

Gerbils are submitted to bilateral carotid occlusion for seven minutes under isoflurane anaesthesia and the animals are allowed to recover from anaesthesia. After seven days the gerbils are killed and their brains examined histologically for neuronal damage in the $CA_1$ region of the hippocampus.

B. Rat two vessel occlusion plus hypotension model

Rats, under nitrous oxide anaesthesia, are submitted to ten minutes of cerebral ischaemia by a combination of bilateral carotid occlusion and reduction of arterial blood pressure to 50 mm Hg. Onset of ischaemia is defined as the time of cessation of EEG activity, normally within 1 minute after clamping. At the end of the ischaemia period the vascular clamps are removed, the withdrawn blood is re-infused, and the rats are allowed to recover. They are killed at 7 days and their brains examined histologically for neuronal damage in the cerebral cortex and dorsal hippocampus. The procedure is a modification of a method described by M. L. Smith et al. Acta Neurol, Scand., 1984, 69, 385–401.

We claim:

1. A method of protecting against neuronal damage resulting from cerebral ischaemia in a mammal which comprises administering to a mammal in need of said protection an effective amount of a compound of formula (I) or a physiologically acceptable salt or hydrate thereof

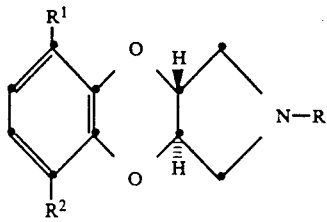

wherein

R is a hydrogen atom or a group selected from $C_1$-$C_6$alkyl, $C_1$-$C_6$alkyl substituted by a $C_3$-$C_7$cycloalkyl), $C_3$-$C_6$alkenyl, $C_3$-$C_6$alkynyl, $C_3$-$C_7$cycloakyl aralkyl (in which the alkyl moiety contains 1 to 5 carbon atoms) and CHO;

$R^1$ is a halogen atom or a group selected from $C_1$-$C_4$alkyl, $C_1$-$C_4$alkoxy, hydroxyl, cyano, nitro and —$NR^3R^4$;

$R^2$ is a hydrogen atom, a halogen atom of a group selected from $C_1$-$C_4$alkyl $C_1$-$C_4$alkoxy, hydroxyl, cyano, nitro and —$NR^3R^4$;

$R^3$ is a hydrogen atom or a $C_1$-$C_4$alkyl group; and $R^4$ is a hydrogen atom or a $C_1$-$C_4$alkyl group.

2. A method according to claim 1 wherein

R is a hydrogen atom, $R^1$ is a fluorine atom, and $R^2$ is a hydrogen atom.

3. A method according to claim 2 which comprises administering to a mammal in need of said protection an effective amount of (±)-trans-5-fluoro-2,3,3a,9a-tetrahydro-1H-[1,4]-benzodioxino[2,3-c]pyrrole hydrochloride.

4. A method according to claim 3 which comprises administering to a mammal in need of said protection an effective amount of (±)-trans-5-fluoro-2,3,3a,9a-tetrahydro-1H-[1,4]-benzodioxino[2,3-c]pyrrole hydrochloride hemihydrate.

5. A method according to claim 1, wherein the mammal is man.

6. A method according to claim 2, wherein the mammal is man.

7. A method according to claim 3, wherein the mammal is man.

8. A method according to claim 4, wherein the mammal is man.

UNITED STATES PATENT AND TRADEMARK OFFICE
CERTIFICATE OF CORRECTION

PATENT NO. : 5,010,096
DATED : April 23, 1991
INVENTOR(S) : Ann G. Hayes, et al.

It is certified that error appears in the above-identified patent and that said Letters Patent is hereby corrected as shown below:

Column 5, line 29, after the letters "kyl", delete ")".

Colunm 6, line 4, after the word "atom" change "of" to -- or --.

Signed and Sealed this

Fifth Day of October, 1993

BRUCE LEHMAN

*Attest:*

*Attesting Officer*     *Commissioner of Patents and Trademarks*